(12) United States Patent
Luo

(10) Patent No.: US 11,414,367 B2
(45) Date of Patent: Aug. 16, 2022

(54) METHOD OF PREPARING AND METHOD OF USING TETRACARBONYL CYCLOBUTENE DIHYDRATE COMPOUND

(71) Applicant: Intelligent Manufacturing Technology Research Institute, Hefei University of Technology, Hefei (CN)

(72) Inventor: Mei Luo, AnHui (CN)

(73) Assignee: INIELLIGENT MANUFACTURING TECHNOLOGY RESEARCH INSTITUTE, HEFEI UNIVERSITY OF TECHNOLOGY, Hefei (CN)

( * ) Notice: Subject to any disclaimer, the term of this patent is extended or adjusted under 35 U.S.C. 154(b) by 0 days.

(21) Appl. No.: 17/518,190

(22) Filed: Nov. 3, 2021

(65) Prior Publication Data

US 2022/0144743 A1    May 12, 2022

(30) Foreign Application Priority Data

Nov. 10, 2020   (CN) .......................... 202011247410.8

(51) Int. Cl.
 *C07C 45/29*     (2006.01)
 *C07C 49/39*     (2006.01)

(52) U.S. Cl.
 CPC .......... *C07C 45/29* (2013.01); *C07C 2601/04* (2017.05)

(58) Field of Classification Search
 CPC ........ C07C 45/29; C07C 49/293; C07C 49/39
 See application file for complete search history.

(56) References Cited

PUBLICATIONS

Rodes et al. On the electrochemical behaviour of squaric acid on Pt(hkl) electrodes in acid solutions: a voltammetric and in situ FTIRS study. Journal of Electroanalytical Chemistry 421, 195-204. (Year: 1997).*

* cited by examiner

*Primary Examiner* — Sikarl A Witherspoon
(74) *Attorney, Agent, or Firm* — Muncy, Geissler, Olds & Lowe, P.C.

(57) ABSTRACT

A tetracarbonyl cyclobutene dihydrate compound, having a chemical formula (I).

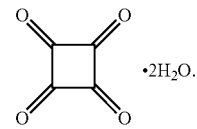

A method of synthesizing the tetracarbonyl cyclobutene dihydrate compound, includes: a synthesis step, a separation step, and a purification step. The synthesis step includes: collecting and dissolving 0.5728 g of squaric acid, 2.7948 g of ammonium formate, and 0.0480 g of the palladium complex in 100 mL of anhydrous methanol, heating and stirring a resulting mixture to reflux for 48 hrs, and stopping the reaction. The separation step includes: performing column chromatography analysis on reaction products according to a volume ratio of dichloromethane to anhydrous methanol of 8:2, to obtain a target product. A method of using the tetracarbonyl cyclobutene dihydrate compound, includes: using tetracarbonyl cyclobutene dihydrate compound as a catalyst in addition reaction between ethyl pyruvate and nitromethane, where a conversion rate of ethyl pyruvate reaches 96.1%.

4 Claims, 1 Drawing Sheet

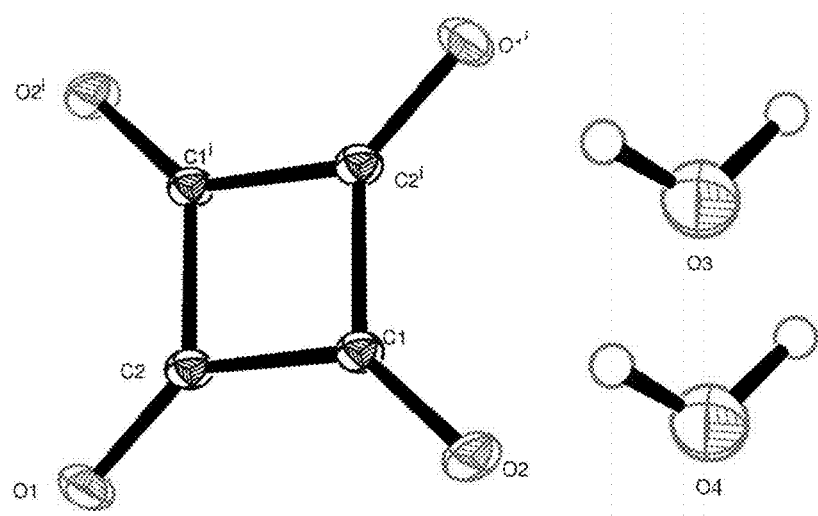

METHOD OF PREPARING AND METHOD OF USING TETRACARBONYL CYCLOBUTENE DIHYDRATE COMPOUND

CROSS-REFERENCE TO RELATED APPLICATIONS

Pursuant to 35 U.S.C. § 119 and the Paris Convention, this application claims the benefit of Chinese Patent Application No. 202011247410.8 filed Nov. 10, 2020, the contents of which are incorporated herein by reference.

TECHNICAL FIELD

The present application relates to a new compound and use thereof, and particular to a method of preparing and a method of using a carbonyl compound, and more particularly to a method of preparing and a method of using a tetracarbonyl cyclobutene dihydrate compound.

BACKGROUND

Tetracarbonyl cyclobutene compound is an important pharmaceutical intermediate. Synthesis and use of the tetracarbonyl cyclobutene compound have been reported in literatures (1-2).

CITED LITERATURES

1. Farnia, Giuseppe; Sandona, Giancarlo; Marcuzzi, Franco, Electrochemical behavior of 1,2-dihydroxycyclo-buten-3,4-dione in dimethyl formamide, Journal of Electroanalytical Chemistry (1993), 348, (1-2), 339-54.
2. Horii, Hideo; Abe, Yasuo; Taniguchi, Setsuo, Absorption spectrum of the squaric acid radical. Chemistry Express (1986), 1, (2), 83-6.

SUMMARY

In view of the above technical problems, it is an objective of the present application to provide a tetracarbonyl cyclobutene dihydrate compound, which is able to obtain the target product by one-step synthesis.

The tetracarbonyl cyclobutene dihydrate compound of the present application is prepared by reacting squaric acid with ammonium acetate and has a structure represented by chemical formula (I).

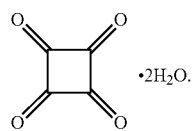

(I)

Chemical name: tetracarbonyl cyclobutene dihydrate compound, herein also called compound (I). The compound has shown good catalytic performance in the Henry reaction of ethyl pyruvate, and a conversion rate of ethyl pyruvate is 96.1%.

The preparation method of the tetracarbonyl cyclobutene dihydrate compound includes a synthesis step and a separation step. The synthesis step comprises: collecting and dissolving 0.5728 g of squaric acid, 2.7948 g of ammonium formate, and 0.0480 g of a palladium complex into 100 mL of anhydrous methanol, heating and stirring a resulting mixture for 48 hrs, and stopping reaction. The separation step comprises: adding 10 mL of 1 M HCl to a resulting reacted mixture, and extracting with dichloromethane 15 mL for three times; combining extracts, washing a resulting first combined extract with 15 mL of 12 M NaOH solution; and extracting with 15 mL of dichloromethane for three times, and combining extracts to yield a second combined extract; and performing rotary evaporation and column chromatography on the second combined extract for separation, whereby obtaining a colorless crystal compound.

The synthesis reaction is shown as follows:

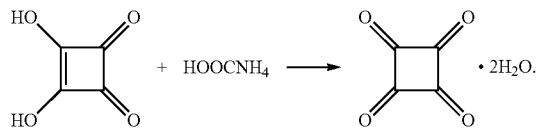

By adopting the synthesis method, the target product can be obtained by one step, the process is simple, and the operation is convenient.

The reaction mechanism of this reaction can be inferred that squaric acid undergoes a series of complex changes from an enol form to a ketone form under combined action of the palladium complex as a catalyst and excess ammonium formate, and the target tetracarbonyl compound is formed.

BRIEF DESCRIPTION OF THE DRAWINGS

The present application is described hereinbelow with reference to accompanying drawings, in which the sole FIGURE is an X-ray diffraction analysis chart of compound I.

DETAILED DESCRIPTION OF THE EMBODIMENTS

To further illustrate the present application, experiments detailing a method of preparing and a method of using a tetracarbonyl cyclobutene dihydrate compound are described below. It should be noted that the following examples are intended to describe and not to limit the present application.

Preparation of a palladium complex is described as follows.

Example 1. Preparation of Chiral Palladium Complex (1) Preparation of [1,4-(4R)-diisopropyl-2-oxazolinyl]benzene 1.4054 g (10.64 mmol) of anhydrous $ZnCl_2$, 40 mL of chlorobenzene, 5.0236 g (39.2 mmol) of 1,4-dicyanobenzene, 16.2075 g of L-valinol were added in a 100 mL two-neck flask under an anhydrous and oxygen-free condition. A resulting mixture was refluxed at a high temperature for 60 hrs. The reaction was stopped, and then a solvent was removed under a reduced pressure to obtain a residue. After that, the residue was dissolved in water and extracted with $CHCl_3$ (20 mL×2). An organic phase was dried by anhydrous sodium sulfate, rotary filtration was then performed to remove the solvent, and a crude product was performed with column chromatography with petroleum ether/dichloromethane (4:1) to obtain a light green viscous liquid with a yield of 52%. An obtained white crystal has a melting point of 48-50° C., $[a]^5{}_D$=+111.9° (c=0.429, CHCl3); $^1$H NMR (500 MHz, CDCl$_3$, 27° C.), δ (ppm)=7.97 (s, 4H), 4.39-4.43 (t, 3.18 Hz, 1H), 4.09-4.15 (m, 2H), 1.85-1.86 (m, 1H), (d, J=6.24 Hz, 6H), 0.86-0.96 (d, J=6.24 Hz, 6H). $^{13}$C NMR 18.13, 19.03, 32.85, 70.26, 72.76, 128.10, 128.16, 130.32, 162.82. IR: 3273, 2976, 2960, 2932, 2889, 2869, 1643, 1512, 1469, 1408, 1382, 1366, 1350, 1320, 1296, 1276, 1214, 1180, 1108, 1077, 1047, 1014, 971, 955, 900, 891, 838, 726, 698, 675, 659, 540. HRMS (EI): m/z (%): calcd for $C_{18}H_{24}N_2O_2$: 300.1838; found: 300.1833.

(2) Preparation of bis{[1,4-(4S)-diisopropyl-2-oxazolinylbenzene]palladium Chloride} Complex 1.5603 g (4.92 mmol) of palladium chloride, 1.0435 g (3.48 mmol) of 1,4-(4R)-diisopropyl-2-oxazolinylbenzene, and 30 mL of chlorobenzene were added to a 100 mL two-neck flask under an anhydrous and oxygen-free condition. A resulting mixture was refluxed at a high temperature for 48 hrs. The reaction was then stopped, and a solvent was removed under a reduced pressure. A resulting residue chloroform and ethanol were dissolved and naturally volatized to obtain a crystal of a reddish-brown complex, with a yield of 92%. m.p.: >200° C., $[a]^5{}_D$=+512.8° (c 0.0564, CH3OH); $^1$H NMR (600 MHz, CDCl$_3$), δ' ppm 8.81 (s, 8H, ArH), 4.61-4.63 (m, 4H, CH×4), 4.53 (t, J=9.6 Hz, 4H, CH×4), 4.44 (t, J=8.5 Hz, 4H, CH×4), 3.07-3.10 (m, 4H), 1.18 and 1.15 (dd, J=6.7, 7.2 Hz, 24H, CH3×4); $^{13}$C NMR (150 MHz, CDCl$_3$) δ ppm 166.8, 130.1 (×2), 129.3, 72.0, 69.1, 30.7, 19.0, 15.6; $v_{max}$ (cm$^{-1}$) 3487, 3049, 2957, 2929, 2872, 1642, 1609, 1572, 1509, 1480, 1464, 1416, 1379, 1331, 1288, 1246, 1178, 1141, 1123, 1099, 1045, 1018, 959, 933, 899, 854, 804, 770, 722, 693, 438. Elemental analysis: $C_{36}H_{48}N_4Cl_4O_4Pd_2$: Test value: C, 45.26%, H, 5.06%, and N, 5.86%; and theoretical value: C, 45.32%, H, 5.24%, and N, 5.48%.

Example 2 Preparation of Tetracarbonyl Compound 0.5728 g of squaric acid, 2.7948 g of ammonium formate, and 0.0480 g of the palladium complex were collected and dissolved in 100 mL of anhydrous methanol. A resulting mixture was heated and stirred to reflux for 48 hrs, and the reaction was then stopped. Reaction products were performed with column chromatography analysis according to a volume ratio of dichloromethane to anhydrous methanol of 8:2 to obtain 0.3481 g of a target product, the yield was 68%, and a melting point of the target product was >250° C. Elemental analysis: (C4H4O6); theoretical value: 32.45% of C and 2.72% of H; and measured value: 32.67% of C and 2.68% of H; HRMS: Theoretical value: 148.0008; Measured value: 148.0012; 13CNMR (125 MHz, CDCl3, 27° C.): 196.5, IR (KBr): 3019, 2854, 2177, 1652, 1500, 1418, 1364, 1088.

| Crystal data of the compound | |
|---|---|
| Empirical formula | C4H4O6 |
| Molecular weight | 148.07 |
| Temperature | 291(2) K |
| wavelength | 0.71073 Å |
| Crystal system, space group | Monoclinic, C 2/c |
| Unit cell dimensions | a = 3.70690(10) Å alpha = 90 deg. |
| | b = 7.2586(3) Å beta = 97.897 deg. |
| | c = 11.9274(5) Å gamma = 90 deg. |
| volume | 317.71 (2) Å$^3$ |
| charge density | 2 , 1.548 Mg/m$^3$ |
| Absorption correction parameter | 1.376 mm$^{-1}$ |
| Number of electrons in a unit cell | 152.0 |
| Crystal size | 0.220 × 0.180 × 0.170 mm |
| Theta range | 14.322 to 139.478 |
| Collection range of HKL's indicator | −3 <= h <= 4, −8 <= k < 8, −14 <= 1 <= 14 |
| Reflections collected/unique | 998/583 [R(int) = 0.0162] |
| Completeness to theta = 30.5 | 1.098% |
| Absorption correction method | Multi-layer scanning |
| Maximum and minimum transmittance | 0.7456 and 0.5760 |
| Refinement method | Full-matrix least-square on F$^2$ |
| Data number/restraint number/parameter number | 583/2/54 |
| Refinement method | 1.098 |
| Uniformity factor of diffraction point | $R_1$ = 0.0678, $wR_2$ = 0.1678 |
| Observable diffraction fit factor | $R_1$ = 0.0702, $wR_2$ = 0.1693 |
| Largest peak and hole on the difference Fourier diagram | 0.610 and −0.55 e.Å$^{-3}$ |

TABLE 4

Typical bond length data of crystal
Bond Lengths for LM-200915.

| Atom | Atom | Length/Å | Atom | Atom | Length/Å |
|---|---|---|---|---|---|
| O1 | C2 | 1.252(4) | C1 | C2 | 1.465(4) |
| O2 | C1 | 1.257(4) | C2 | C1$^1$ | 1.462(4) |
| C1 | C2$^1$ | 1.462(4) | | | |

Bond angle data of crystal

| Atom | Atom | Atom | Angle/° | Atom | Atom | Atom | Angle/° |
|---|---|---|---|---|---|---|---|
| O2 | C1 | C2$^1$ | 133.8 (3) | O1 | C2 | C1$^1$ | 133.7 (3) |
| O2 | C1 | C2 | 136.1 (3) | O1 | C2 | C1 | 136.4 (3) |
| C2$^1$ | C1 | C2 | 90.2 (2) | C1$^1$ | C2 | C1 | 89.8 (2) |

Example 3 Application in Henry Reaction

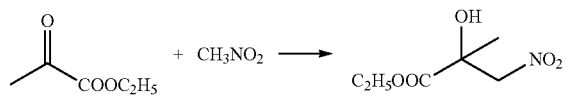

0.05 mmol of the compound (I) was placed in a 25 mL flask, and 1 mL tetrahydrofuran, 0.3 mL nitromethane and 0.5 mmol of ethyl pyruvate were added sequentially to the flask, a resulting mixture were stirred for reaction for 20 hrs. Samples were taken for $^1$HNMR detection. The conversion rate was 96.1%; $^1$H NMR (600 MHz, CDCl3): δ) 4.86 (d, J=13.8 Hz, 1H), 4.58 (d, J=13.8 Hz, 1H), 4.34 (m, 2H), 3.85 (s, 1H), 1.46 (s, 3H), 1.33 (t, J=7.2 Hz, 3H). 13 C NMR (150 MHz, CDCl 3): δ=173.4, 80.9, 72.4, 63.0, 23.8, 13.9.

What is claimed is:

1. A tetracarbonyl cyclobutene dihydrate compound, prepared by reacting squaric acid with ammonium formate, and having a chemical formula (I):

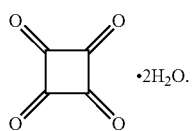 ·2H₂O.    (I)

2. The tetracarbonyl cyclobutene dihydrate compound of claim 1, prepared into a form of a crystal, wherein
when being diffracted with a MoKα ray, which is monochromated by a graphite monochromator and has a wavelength of λ=0.71073 Å, in an ω-θ scanning mode on an Oxford X-ray single crystal diffractometer at a temperature of 293(2)K, the crystal of the tetracarbonyl cyclobutene dihydrate compound belongs to a monoclinic system, C 2/c, and has unit cell dimensions as follows: a=3.70690(10) Å alpha=90 deg.; b=7.2586(3) Å beta=97.897 deg.; and c=11.9274(5) Å gamma=90 deg.

3. A method of synthesizing the tetracarbonyl cyclobutene dihydrate compound of claim 1, comprising: a synthesis step, a separation step, and a purification step; wherein
the synthesis step comprises: collecting and dissolving 0.5728 g of squaric acid, 2.7948 g of ammonium formate, and 0.0480 g of a palladium complex in 100 mL of anhydrous methanol, heating and stirring a resulting mixture to reflux for 48 hrs, and stopping the reaction; and
the separation step comprises: performing column chromatography analysis on reaction products according to a volume ratio of dichloromethane to anhydrous methanol of 8:2, to obtain a target product.

4. A method of using the tetracarbonyl cyclobutene dihydrate compound of claim 1, as a catalyst in addition reaction between ethyl pyruvate and nitromethane; wherein a conversion rate of ethyl pyruvate reaches 96.1%.

* * * * *